US008338123B2

(12) United States Patent
Plomp et al.

(10) Patent No.: US 8,338,123 B2
(45) Date of Patent: Dec. 25, 2012

(54) FOOD PRODUCTION PROCESS

(75) Inventors: Pieter Jan Arnoldus Maria Plomp, Delft (NL); Lex De Boer, Wateringen (NL); Rutger Jan Van Rooijen, Ede (NL); Roelf Bernhard Meima, Kamerik (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/333,129

(22) Filed: Dec. 21, 2011

(65) Prior Publication Data

US 2012/0141629 A1 Jun. 7, 2012

Related U.S. Application Data

(62) Division of application No. 10/538,000, filed as application No. PCT/EP03/14553 on Dec. 18, 2003, now Pat. No. 8,105,815.

(30) Foreign Application Priority Data

Dec. 19, 2002 (EP) .................................... 02102819

(51) Int. Cl.
*C12Q 1/34* (2006.01)
*A23J 3/34* (2006.01)
*C12N 9/82* (2006.01)
*C12P 21/00* (2006.01)
*C07K 14/00* (2006.01)

(52) U.S. Cl. ......... 435/18; 435/229; 435/69.1; 530/350; 426/656

(58) Field of Classification Search .................. 435/229, 435/18, 320.1, 252.3, 69.1; 530/350
See application file for complete search history.

(56) References Cited

U.S. PATENT DOCUMENTS

| | | | |
|---|---|---|---|
| 5,310,670 | A | 5/1994 | Goward |
| 6,989,167 | B2 | 1/2006 | Howie et al. |
| 7,037,540 | B2 | 5/2006 | Elder et al. |
| 7,189,422 | B2 | 3/2007 | Howie et al. |
| 7,220,440 | B2 | 5/2007 | Dria et al. |
| 7,264,838 | B2 | 9/2007 | Plank et al. |
| 7,267,834 | B2 | 9/2007 | Elder et al. |
| 7,393,550 | B2 | 7/2008 | Barry et al. |
| 7,396,670 | B2 | 7/2008 | Budolfsen et al. |

FOREIGN PATENT DOCUMENTS

| | | |
|---|---|---|
| WO | 2004/026042 | 4/2004 |
| WO | 2004/026043 | 4/2004 |
| WO | 2004/032648 | 4/2004 |

OTHER PUBLICATIONS

Ausubel, F., "Hybridization Analysis of DNA Blots", Current Protocols in Molecular Biology (1993), pp. 2.10.8-2.10.11, Supplement 21.
Branden et al., "Introduction to Protein Structure—Prediction, Engineering, and Design of Protein Structures", Garland Publishing Inc., New York, 1991, p. 247.
Witkowski et al., "Conversion of a Beta-Ketoacyl Synthase to a Malonyl Decarboxylase by Replacement of the Active-Site Cysteine with Glutamine", Biochemistry, 1999, vol. 38, pp. 11643-11650.
Seffernick et al., "Melamine Deaminase and Atrazine Chlorohydrolase: 98 Percent Identical But Functionally Different", Journal of Bacteriology, Apr. 2001, vol. 183, No. 8, pp. 2401-2410.
Minton et al., PIR accession No. A26054, 1999.
Louboudy, S., "Purification and Properties of L-asparaginase Produced by *Asperfillus niger*, S-48 TAT, the Casual Fungus of Biodeterioration Inside Tut Ankhamen Tomb (TAT)", Egyptian Journal of Biotechnology, (1998), vol. 4, pp. 110-123.
Atkinson et al., "Production of L-asparaginase", Database EMBL Accession No. A14577, Jan. 1994.
Friedman, "Chemistry, Biochemistry, and Safety of Acrylamide", J. Agric. Food Chem., 15:4504-4526, Jul. 2003.
Lingnert et al., "Acrylamide in Food: Mechanisms of Formation and Influencing Factors During Heating of Foods", Scan. J. Nutr., 46:159-172, Dec. 2002.
Mottram et al., "Acrylamide Is Formed in the Maillard Reaction", Nature, 419:448-449, Oct. 2002.
Prista et al., "L-asparaginase of Thermus Thermophilus: Purification, Properties and Identification of Essential Amino Acids for its Caralytic Activity", Mol. Cell. Biochem., 216:93-101, Jan. 2001.
Stadler et al., "Acrylamide from Maillard Reaction Products", Nature, 419:449, Oct. 2002.
Working Group 1 "Mechanisms of Formation of Acrylamide in Food: Background", 24 pages., see www.jifsan.umd.edu/acrylamide2002.htm, Oct. 2002.
Zyzak et al., "Acrylamie Formation Mechanisms in Heated Foods", J. Agric. Food Chem., 15:4782-4787, Jun. 2003.
International Search Report for PCT/EP2003/014553, six pages, Jun. 2004.
International Preliminary Examination Report for PCT/EP2003/014553, seven pages, Jun. 2004.

*Primary Examiner* — Delia Ramirez
(74) *Attorney, Agent, or Firm* — Baker Donelson Bearman, Caldwell & Berkowitz, PC

(57) ABSTRACT

Process for the production of a food product involving at least one heating step, comprising adding one or more enzymes to an intermediate form of said food product in said production process whereby the enzyme is added prior to said heating step in an amount that is effective in reducing the level of amino acids that are present in said intermediate form of said food product which amino acids are involved in the formation of acrylamide during said heating step. The invention also relates to food products obtained from the process of the invention.

11 Claims, No Drawings

SEQUENCE LISTING

<160> NUMBER OF SEQ ID NOS: 3

<210> SEQ ID NO 1
<211> LENGTH: 3223
<212> TYPE: DNA
<213> ORGANISM: Aspergillus niger

<400> SEQUENCE: 1

```
tgggggggaac ttgcatctga gagcatcata ctagttacta ctactactac tacttgccga      60
tgaataaaca tcctgcttgt actacgcatc gccgtcttgc tgacatggag atatattttg     120
ggctccgaga gttttgatag cagtagccaa ttaactagta gatgctagta ctactctagt     180
aatttggggg cgaatgttga atccagctca tgccaattga catctggaga tctccacgag     240
acaacgagat aagatgaaat attgctgtca tgggtgataa ctagatgctt cgagaaggat     300
tcttgaggat tgcctcatcg catgggataa tatcaccctc gggtggacct tcccggctgt     360
tggggcttat cgtggaagag tcacccccga tatcggtggg ccaagccctt tatcaatcat     420
catcctatca gtttccaccc acaagatagc ctatggaccc tgattccctt ctagccacag     480
agactagtac tagtctatca tgtcgactcc atgtggagaa accctgataa gaccatgtgg     540
aggaggagat agcaagcctc cacagaaaca atatcatctc cacctgcaat cacggttgga     600
ttccgaatac acccgccgcc tggcaagcac atggggtata aaatgctgaa accaggcaag     660
atgaattgga agagaagcca gcagagacca tcgcatccgt cttcatcatg cctctcaagc     720
cgattctcct gtctgccctg gccagtctcg cctcggcctc tccgctgctc tactcgcgga     780
```

```
ccaccaatga aaccttcgtc ttcaccaatg ccaatggcct caacttcacc cagatgaaca    840
ccaccctgcc gaacgtgacc attttcgcaa cgggtaggtg gaccgagtat acctcaggta    900
gtgcgaccga tagttaaccg caactcacag gtggtaccat cgcgggctcc gattccagct    960
caaccgccac gaccggctac acctccgag cagtcgggt cctgtccctc atcgatgcgg     1020
tgccatccat gctggatgtg gccaatgttg ccggcgtcca ggtggccaac gtgggaagcg    1080
aggatatcac ctctgacatc ctgatttcca tgtccaagaa gctgaaccgc gttgtatgtg    1140
aggacccgac catggccggt gctgtcatca cccacggcac cgacaccctc gaggagactg    1200
ccttcttcct ggacgccact gtcaactgtg caagccaat tgtcatcgtg ggtgccatgc     1260
gcccatccac ggccatctca gctgacgggc ccttcaatct gctcgaagcc gtgacggtgg    1320
ctgcctccac gtcggcgcgc gatcgcggtg ccatggtggt catgaacgat cgcattgcct    1380
cggcctacta tgtgaccaag accaatgcca acactatgga caccttcaag gccatggaga    1440
tgggctacct tggcgagatg atctccaaca ccccttctt cttctacccg cccgtcaagc     1500
caaccggtaa ggtggccttt gacatcacca acgtgactga gatccccgt gtggacattc     1560 tgttttctta tgaggacatg cacaacgaca ccctctacaa cgccatctcc agtggtgccc    1620
agggaattgt ggtgagtgtg atttccttga tctctctcta taaaacttgg aatggacgct    1680
gatgagaata gattgccggg gctggtgctg gaggcgtcac aacctccttc aatgaggcta    1740
tcgaggatgt catcaaccgt ttggagatcc ctgtcgtgca gagtatgcgc acagtcaatg    1800
gggaagtgcc actgtcagac gtgagcagcg acaccgccac ccacatcgcc agtggatacc    1860
taaacccgca gaagtcccgc attcgttgg gattgctgct atcccaggga agaatatca     1920 ccgaaatcgc tgacgtgttt gctctgggca cggatgcgta ggtgtcgata gaaccattgt    1980
atataataat gaccggatat tatgatcatg atagattgca atagaaagtg actggataca    2040
catcagcaaa ggataccgag ttttgccctc aggcgttcgt agaaaaagtg tatcctactg    2100
aagatcatga atcatgtctt atcttctggc cccctcgtat ccagggtgtt ggacatgcag    2160
ggtgctttgc gtctgaagga tccgagatca aattgacacg agccagagtc tgatacatcc    2220
ataatagtgg gtatatttga agtccattga tagtccttgt ttgtgtcggg caattgggtt    2280
agctagggcc tggcttggtg gcatatcgtt ggactaatag atggtagttc aattaccgac    2340
gggactgtct cccgccatta ttctcacaat tcttatcagc acatttccc tgtcgcgctt     2400 ggatctgcaa tatttatttc cctcgtcatc acattcccac gaaaagacca tccagacatc    2460
ttgctcggta ttctggaccg taagactgtt ttgaaaggca aatgtaaagc gtgattggtc    2520
gacgtcaagc ctgaccaatc tagtaagctg gtcttacttt gggtgtagac ggaggtatta    2580
ggtagtatta aggcagctag ttcgcctgca ttaccaccca ggcgaggcac gccactgctg    2640
atcaggcgcg aaatgaacg aagtgcgagg tccacttaac atgatgcgcg cggatactaa      2700
ggcgaccaag accctggatt gatcgctatg attcgcggaa ccccgcgggt tcttcacggc    2760
tttcgataac gcaggattgg atcctcccag cctcgtctct gcaagtggga ccctgaaggg    2820
ctctcctgca cgtcattact cagacactcc catcttttgc ttatttgcaa tgaatcttat    2880
gggctgaccc tcagctcggc gtgggatgcc tgaatcgttg gtgaaagtct atttgagcaa    2940
tcctagcctg ctggtagagg cggatgatta taataatcaa agcaccctat cgtaaggatg    3000
aaggcttgtc cctggtcaac catcactctg gttattgact agttgtgttt gggagacagc    3060
tgaagcccat tgtcggtaat cgtccccaaa gaatctgccc ctgcatcatg gagtcaggaa    3120
```

```
agaccgggtt tcgcacggtc gcagaaccgc atccaacacg tctagtagaa ggaggggtag    3180
ggatactcat ccgtctattg tgtatatctg caacgactaa tgt                     3223

<210> SEQ ID NO 2
<211> LENGTH: 1137
<212> TYPE: DNA
<213> ORGANISM: Aspergillus niger
<220> FEATURE:
<221> NAME/KEY: CDS
<222> LOCATION: (1)..(1137)

<400> SEQUENCE: 2 atg cct ctc aag ccg att ctc ctg tct gcc ctg gcc agt ctc gcc tcg    48
Met Pro Leu Lys Pro Ile Leu Leu Ser Ala Leu Ala Ser Leu Ala Ser
1               5                   10                  15 gcc tct ccg ctg ctc tac tcg cgg acc acc aat gaa acc ttc gtc ttc    96
Ala Ser Pro Leu Leu Tyr Ser Arg Thr Thr Asn Glu Thr Phe Val Phe
            20                  25                  30 acc aat gcc aat ggc ctc aac ttc acc cag atg aac acc acc ctg ccg   144
Thr Asn Ala Asn Gly Leu Asn Phe Thr Gln Met Asn Thr Thr Leu Pro
        35                  40                  45 aac gtg acc att ttc gca acg ggt ggt acc atc gcg ggc tcc gat tcc   192
Asn Val Thr Ile Phe Ala Thr Gly Gly Thr Ile Ala Gly Ser Asp Ser
    50                  55                  60 agc tca acc gcc acg acc ggc tac acc tcc gga gca gtc ggg gtc ctg   240
Ser Ser Thr Ala Thr Thr Gly Tyr Thr Ser Gly Ala Val Gly Val Leu
65                  70                  75                  80 tcc ctc atc gat gcg gtg cca tcc atg ctg gat gtg gcc aat gtt gcc   288
Ser Leu Ile Asp Ala Val Pro Ser Met Leu Asp Val Ala Asn Val Ala
                85                  90                  95 ggc gtc cag gtg gcc aac gtg gga agc gag gat atc acc tct gac atc   336
Gly Val Gln Val Ala Asn Val Gly Ser Glu Asp Ile Thr Ser Asp Ile
            100                 105                 110 ctg att tcc atg tcc aag aag ctg aac cgc gtt gta tgt gag gac ccg   384
Leu Ile Ser Met Ser Lys Lys Leu Asn Arg Val Val Cys Glu Asp Pro
        115                 120                 125 acc atg gcc ggt gct gtc atc acc cac ggc acc gac acc ctc gag gag   432
Thr Met Ala Gly Ala Val Ile Thr His Gly Thr Asp Thr Leu Glu Glu
    130                 135                 140 act gcc ttc ttc ctg gac gcc act gtc aac tgt ggc aag cca att gtc   480
Thr Ala Phe Phe Leu Asp Ala Thr Val Asn Cys Gly Lys Pro Ile Val
145                 150                 155                 160 atc gtg ggt gcc atg cgc cca tcc acg gcc atc tca gct gac ggg ccc   528
Ile Val Gly Ala Met Arg Pro Ser Thr Ala Ile Ser Ala Asp Gly Pro
                165                 170                 175 ttc aat ctg ctc gaa gcc gtg acg gtg gct gcc tcc acg tcg gcg cgc   576
Phe Asn Leu Leu Glu Ala Val Thr Val Ala Ala Ser Thr Ser Ala Arg
            180                 185                 190 gat cgc ggt gcc atg gtg gtc atg aac gat cgc att gcc tcg gcc tac   624
Asp Arg Gly Ala Met Val Val Met Asn Asp Arg Ile Ala Ser Ala Tyr
        195                 200                 205 tat gtg acc aag acc aat gcc aac act atg gac acc ttc aag gcc atg   672
Tyr Val Thr Lys Thr Asn Ala Asn Thr Met Asp Thr Phe Lys Ala Met
    210                 215                 220 gag atg ggc tac ctt ggc gag atg atc tcc aac acc cct ttc ttc ttc   720
Glu Met Gly Tyr Leu Gly Glu Met Ile Ser Asn Thr Pro Phe Phe Phe
225                 230                 235                 240 tac ccg ccc gtc aag cca acc ggt aag gtg gcc ttt gac atc acc aac   768
Tyr Pro Pro Val Lys Pro Thr Gly Lys Val Ala Phe Asp Ile Thr Asn
                245                 250                 255
```

```
gtg act gag atc ccc cgt gtg gac att ctg ttt tct tat gag gac atg      816
Val Thr Glu Ile Pro Arg Val Asp Ile Leu Phe Ser Tyr Glu Asp Met
        260                 265                 270 cac aac gac acc ctc tac aac gcc atc tcc agt ggt gcc cag gga att      864
His Asn Asp Thr Leu Tyr Asn Ala Ile Ser Ser Gly Ala Gln Gly Ile
    275                 280                 285 gtg att gcc ggg gct ggt gct gga ggc gtc aca acc tcc ttc aat gag      912
Val Ile Ala Gly Ala Gly Ala Gly Gly Val Thr Thr Ser Phe Asn Glu
290                 295                 300 gct atc gag gat gtc atc aac cgt ttg gag atc cct gtc gtg cag agt      960
Ala Ile Glu Asp Val Ile Asn Arg Leu Glu Ile Pro Val Val Gln Ser
305                 310                 315                 320 atg cgc aca gtc aat ggg gaa gtg cca ctg tca gac gtg agc agc gac     1008
Met Arg Thr Val Asn Gly Glu Val Pro Leu Ser Asp Val Ser Ser Asp
            325                 330                 335 acc gcc acc cac atc gcc agt gga tac cta aac ccg cag aag tcc cgc     1056
Thr Ala Thr His Ile Ala Ser Gly Tyr Leu Asn Pro Gln Lys Ser Arg
        340                 345                 350 att ctg ttg gga ttg cta ctg tcc cag gga aag aat atc acc gaa atc     1104
Ile Leu Leu Gly Leu Leu Leu Ser Gln Gly Lys Asn Ile Thr Glu Ile
    355                 360                 365 gct gac gtg ttt gct ctg ggc acg gat gcg tag                         1137
Ala Asp Val Phe Ala Leu Gly Thr Asp Ala
370                 375

<210> SEQ ID NO 3
<211> LENGTH: 378
<212> TYPE: PRT
<213> ORGANISM: Aspergillus niger

<400> SEQUENCE: 3

Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe
            20                  25                  30

Thr Asn Ala Asn Gly Leu Asn Phe Thr Gln Met Asn Thr Thr Leu Pro
        35                  40                  45

Asn Val Thr Ile Phe Ala Thr Gly Gly Thr Ile Ala Gly Ser Asp Ser
    50                  55                  60

Ser Ser Thr Ala Thr Thr Gly Tyr Thr Ser Gly Ala Val Gly Val Leu
65                  70                  75                  80

Ser Leu Ile Asp Ala Val Pro Ser Met Leu Asp Val Ala Asn Val Ala
                85                  90                  95

Gly Val Gln Val Ala Asn Val Gly Ser Glu Asp Ile Thr Ser Asp Ile
            100                 105                 110

Leu Ile Ser Met Ser Lys Lys Leu Asn Arg Val Val Cys Glu Asp Pro
        115                 120                 125

Thr Met Ala Gly Ala Val Ile Thr His Gly Thr Asp Thr Leu Glu Glu
    130                 135                 140

Thr Ala Phe Phe Leu Asp Ala Thr Val Asn Cys Gly Lys Pro Ile Val
145                 150                 155                 160

Ile Val Gly Ala Met Arg Pro Ser Thr Ala Ile Ser Ala Asp Gly Pro
                165                 170                 175

Phe Asn Leu Leu Glu Ala Val Thr Val Ala Ala Ser Thr Ser Ala Arg
            180                 185                 190

Asp Arg Gly Ala Met Val Val Met Asn Asp Arg Ile Ala Ser Ala Tyr
        195                 200                 205
```

-continued

```
Tyr Val Thr Lys Thr Asn Ala Asn Thr Met Asp Thr Phe Lys Ala Met
    210             215             220
Glu Met Gly Tyr Leu Gly Glu Met Ile Ser Asn Thr Pro Phe Phe Phe
225             230             235                         240
Tyr Pro Pro Val Lys Pro Thr Gly Lys Val Ala Phe Asp Ile Thr Asn
            245             250                 255
Val Thr Glu Ile Pro Arg Val Asp Ile Leu Phe Ser Tyr Glu Asp Met
            260             265             270
His Asn Asp Thr Leu Tyr Asn Ala Ile Ser Ser Gly Ala Gln Gly Ile
        275             280             285
Val Ile Ala Gly Ala Gly Ala Gly Gly Val Thr Thr Ser Phe Asn Glu
    290             295             300
Ala Ile Glu Asp Val Ile Asn Arg Leu Glu Ile Pro Val Val Gln Ser
305             310             315                         320
Met Arg Thr Val Asn Gly Glu Val Pro Leu Ser Asp Val Ser Ser Asp
            325             330             335
Thr Ala Thr His Ile Ala Ser Gly Tyr Leu Asn Pro Gln Lys Ser Arg
            340             345             350
Ile Leu Leu Gly Leu Leu Leu Ser Gln Gly Lys Asn Ile Thr Glu Ile
        355             360             365
Ala Asp Val Phe Ala Leu Gly Thr Asp Ala
    370             375
```

FOOD PRODUCTION PROCESS

CROSS REFERENCE TO RELATED APPLICATIONS

This application is a Divisional of application Ser. No. 10/538,000, filed Jun. 9, 2005, now U.S. Pat. No. 8,105,815, which is a §371 National Stage Application of PCT/EP2003/014553 filed Dec. 18, 2003 which designated the U.S. and claims benefit of EP 02102819.6, dated Dec. 19, 2002, the entire content of which is hereby incorporated by reference.

The present invention relates to a process for the production of a food product involving at least one heating step and food products obtained thereof. Furthermore, the present invention relates to a novel enzyme suitable for the process according to the invention and to newly identified polynucleotide sequences comprising genes that encode the novel enzyme.

Acrylamide has been produced commercially for a long time for a variety of technical applications and therefore, its toxicological background is well evaluated. Acrylamide is used for the production of polyacrylamide, and the latter compound is applied in the production of drinking water, soil stabilization, industrial wastewater treatment, the winning of oil and laboratory applications.

Acrylamide is considered as probably carcinogenic for animals and humans. In 1991 the Scientific Committee on Food has investigated monomeric acrylamide in contact food materials and in its evaluation it was concluded that acrylamide is a genotoxic carcinogen. Bergmark et al. (Chem. Res. Toxicol., 10, 78-84 (1997)) demonstrated that acrylamide is also a component in tobacco smoke and this was the first link between the formation of acrylamide and the heating of biological material. Recently, the occurrence of acrylamide in a number of food and oven prepared foods was published (Tareke et al. Chem. Res. Toxicol. 13, 517-522. (2000)) and this resulted in world-wide concern. Further research revealed that considerable amounts of acrylamide are detectable in a variety of baked, fried and oven prepared common foods and it was demonstrated that the occurrence of acrylamide in food was the result of the baking process.

The official limit in the UK for acrylamide contamination in food products is set at 10 ppb (10 micrograms per kilogram) and the values presented above abundantly exceed this value for a lot of products, especially cereals, bread products and potato crisps.

The relation between the administered dose of acrylamide and tumor incidence was observed in animal tests in which rats were fed acrylamide via drinking water and which fate was followed during two years (Friedman, H. L. et. al.), Fundam. Appl. Pharmacol. 85:154-168. M. (1986) and Johnson et. al. Toxicol. Appl. Pharmacol. 85:154-168 (1986)). Chronic toxicity and oncogenicity study on acrylamide in corporated in the drinking water of Fischer 344 rats.

When these data were combined with the results collected in Tareke et. al. in which acrylamide bound to hemoglobin (N-(2-carbamoylethyl)valine) was studied as a function of an acrylamide containing diet to rats, it was calculated that the daily uptake of acrylamide is 1.6 ug acrylamide/kg, corresponding to a cancer risk of $7*10^{-3}$ for humans from life-long exposure.

A pathway for the formation of acrylamide from amino acids and reducing sugars as a result of the Maillard reaction has been proposed Mottram et al. Nature 419:448. (2002). According to this hypothesis, acrylamide may be formed during the Maillard reaction. During baking and roasting, the Maillard reaction is mainly responsible for the color, smell and taste. A reaction associated with the Maillard is the Strecker degradation of amino acids and a pathway to acrylamide was proposed. The formation of acrylamide became detectable when the temperature exceeded 120° C., and the highest formation rate was observed at around 170° C. When asparagine and glucose were present, the highest levels of acrylamide could be observed, while glutamine and aspartic acid only resulted in trace quantities. The fact that acrylamide is formed mainly from asparagine and glucose may explain the high levels acrylamide in oven-cooked or roasted plant based products such as. Several plant raw materials are known to contain substantial levels of asparagine. In potatoes asparagine is the dominant free amino acid is (940 mg/kg, corresponding with 40% of the total amino-acid content) and in wheat flour asparagine is present at a level of circa 167 mg asparagine/kg flour, corresponding with 14% of the total free amino acids pool (Belitz and Grosch in Food Chemistry—Springer New York, 1999).

Therefore, in the interest of public health, there is an urgent need for food products that have substantially lower levels of acrylamide or, preferably, are devoid of it. In first instance, research activities have been initiated in order to unravel the mechanism of acryl amide formation in food products. So far, the results thereof have not yet led to a satisfactory solution of the problem. Secondly, food companies are investigating the possibilities to avoid the formation of acrylamide by lowering the temperature of the oven cooking and roasting processes. Of course, these adaptations will inherently result in food products with altered taste properties (less Maillard products) and these adaptations raise the risk of an enhanced microbial contamination such as by *Salmonella*.

The present invention provides a process for the production of a food product involving at least one heating step, comprising adding one or more enzymes to an intermediate form of said food product in said production process whereby the enzyme is added prior to said heating step in an amount that is effective in reducing the level of amino acids that are present in said intermediate form of said food product which amino acids are involved in the formation of acrylamide during said heating step.

An intermediate form of the food product is defined herein as any form that occurs during the production process prior to obtaining the final form of the food product. The intermediate form may comprise the individual raw materials used and/or mixture thereof and/or mixtures with additives and/or processing aids, or subsequently processed form thereof. For example, for the food product bread, the intermediate forms comprise for example wheat, wheat flour, the initial mixture thereof with other bread ingredients such as for example water, salt, yeast and bread improving compositions, the mixed dough, the kneaded dough, the leavened dough and the partially baked dough.

The food product may be made from at least one raw material that is of plant origin, for example potato, tobacco, coffee, cocoa, rice, cereal, for example wheat, rye corn, maize, barley, groats, buckwheat and oat. Wheat is here and hereafter intended to encompass all known species of the *Triticum* genus, for example aestivum, durum and/or spelta. Also food products made from more than one raw material are included in the scope of this invention, for example food products comprising both wheat (flour) and potato.

Examples of food products in which the process according the invention can be suitable for are any flour based products—for example bread, pastry, cake, pretzels, bagels, Dutch honey cake, cookies, gingerbread, gingercake and crispbread-, and any potato-based products—for example French fries, pommes frites, potato chips, croquettes.

Raw materials as cited above are known to contain substantial amounts of amino acids that are involved in the formation of acrylamide during the heating step of the production process. Alternatively, these amino acids may originate from other sources than the raw materials e.g. from protein hydrolysates, such as yeast extracts, soy hydrolysate, casein hydrolysate and the like, which are used as an additive in the food production process. A preferred production process is the baking of bread and other baked products from wheat flour and/or flours from other cereal origin. Another preferred production process is the deep-frying of potato chips from potato slices.

Preferred heating steps are those at which at least a part of the intermediate food product, e.g. the surface of the food product, is exposed to temperatures at which the formation of acrylamide is promoted, e.g. 110° C. or higher, 120° C. or higher temperatures up to. The heating step in the process according to the invention may be carried out in ovens, for instance at a temperature between 180-220° C., such as for the baking of bread and other bakery products, or in oil such as the frying of potato chips, for example at 160-190° C.

The enzymes used in the process of the invention are preferably enzymes that modify the side chains of amino acids that are involved in the formation of acrylamide during the heating step of the production process and whereby the degradation products of said amino acids are not, or at least to a lesser extent, giving rise to the formation of acrylamide in comparison with the undegraded form of the amino acid. Preferably the enzyme is modifying the side chain of at least one of the amino acids asparagine, glutamine, cystein, methionine, proline, serine, phenylalanine, tyrosine and/or tryptophane. The enzyme may be added as an enzyme preparation or produced in situ by a microorganism capable of producing said enzyme. Preferably the enzyme preparation is derived from a microorganism and obtained by fermentation processes known in the art. The microorganism may be a bacterium, a fungus or a yeast. In a preferred embodiment of the invention, the process comprises the addition of asparaginase (EC 3.5.1.1) or glutaminase (EC 3.5.1.2).

Asparaginase can be obtained from various sources, such as for example from plants, animals and microorganisms, such as for example *Escherichia, Erwinia, Streptomyces, Pseudomonas, Aspergillus* and *Baccillus* species. An example of a suitable *Escherichia* strain is *Escherichia coli*. An example of a suitable *Erwinia* strain is *Erwinia chrysanthemi*. Examples of suitable *Streptomyces* strains are *Streptomyces lividans* or *Streptomyces murinus*. Examples of suitable *Aspergillus* strains are *Aspergillus oryzae, Aspergillus nidulans* or *Aspergillus niger*. Examples of suitable *Bacillus* strains are *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megateruim, Bacillus stearothemophilus, Bacillus subtilis* or *Bacillus thuringiensis*. An example of suitable methods to yield asparaginase from *Bacillus, Streptomyces, Escheria* or *Pseudomonas* strains is described in WO03/083043. WO03/083043 does however not disclose the use of asparaginase to decrease the amount of acrylamide in food as described in the present invention.

Preferably use is made of food-grade organisms, for example *Aspergillus niger* or *Bacillus subtilis*.

In a second aspect, the invention provides newly identified polynucleotide sequences comprising genes that encode a novel asparaginase which for example can be yielded from *Aspergillus niger*. The novel asparaginase can be used in the process for food production of the present invention, for example in production of a baked product from a dough.

Polynucleotides

The invention also provides for novel polynucleotides encoding novel asparaginase enzymes. The present invention provides polynucleotides encoding an asparaginase, tentatively called ASPA01, having an amino acid sequence according to SEQ ID NO: 3 or functional equivalents thereof. The sequence of the gene encoding ASPA01 was determined by sequencing a genomic clone obtained from *Aspergillus niger*. The invention provides polynucleotide sequences comprising the gene encoding the ASPA01 asparaginase as well as its complete cDNA sequence and its coding sequence. Accordingly, the invention relates to an isolated polynucleotide comprising the nucleotide sequence according to SEQ ID NO: 1 or SEQ ID NO: 2 or functional equivalents thereof.

More in particular, the invention relates to an isolated polynucleotide hybridisable under stringent conditions, preferably under highly stringent conditions, to a polynucleotide according to SEQ ID NO: 1 or SEQ ID NO: 2. Advantageously, such polynucleotides may be obtained from filamentous fungi, in particular from *Aspergillus niger*. More specifically, the invention relates to an isolated polynucleotide having a nucleotide sequence according to SEQ ID NO: 1 or SEQ ID NO: 2.

The invention also relates to an isolated polynucleotide encoding at least one functional domain of a polypeptide according to SEQ ID NO: 3 or functional equivalents thereof.

As used herein, the terms "gene" and "recombinant gene" refer to nucleic acid molecules which may be isolated from chromosomal DNA, which include an open reading frame encoding a protein, e.g. an *A. niger* asparaginase. A gene may include coding sequences, non-coding sequences, introns and regulatory sequences. Moreover, a gene refers to an isolated nucleic acid molecule as defined herein.

A nucleic acid molecule of the present invention, such as a nucleic acid molecule having the nucleotide sequence of SEQ ID NO: 1 or SEQ ID NO: 2 or a functional equivalent thereof, can be isolated using standard molecular biology techniques and the sequence information provided herein. For example, using all or portion of the nucleic acid sequence of SEQ ID NO: 1 or the nucleotide sequence of SEQ ID NO: 2 as a hybridization probe, nucleic acid molecules according to the invention can be isolated using standard hybridization and cloning techniques (e. g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO: 1 or SEQ ID NO: 2 can be isolated by the polymerase chain reaction (PCR) using synthetic oligonucleotide primers designed based upon the sequence information contained in SEQ ID NO:1 or SEQ ID NO: 2.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Furthermore, oligonucleotides corresponding to or hybridisable to nucleotide sequences according to the invention can be prepared by standard synthetic techniques, e.g., using an automated DNA synthesizer.

In a preferred embodiment, an isolated nucleic acid molecule of the invention comprises the nucleotide sequence shown in SEQ ID NO: 2. The sequence of SEQ ID NO: 2 corresponds to the coding region of the *A. niger* ASPA01 cDNA. This cDNA comprises sequences encoding the *A. niger* ASPA01 polypeptide according to SEQ ID NO: 3.

In another preferred embodiment, an isolated nucleic acid molecule of the invention comprises a nucleic acid molecule which is a complement of the nucleotide sequence shown in SEQ ID NO:1 or SEQ ID NO: 2 or a functional equivalent of these nucleotide sequences.

A nucleic acid molecule which is complementary to another nucleotide sequence is one which is sufficiently complementary to the other nucleotide sequence such that it can hybridize to the other nucleotide sequence thereby forming a stable duplex.

One aspect of the invention pertains to isolated nucleic acid molecules that encode a polypeptide of the invention or a functional equivalent thereof such as a biologically active fragment or domain, as well as nucleic acid molecules sufficient for use as hybridisation probes to identify nucleic acid molecules encoding a polypeptide of the invention and fragments of such nucleic acid molecules suitable for use as PCR primers for the amplification or mutation of nucleic acid molecules.

An "isolated polynucleotide" or "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

Another embodiment of the invention provides an isolated nucleic acid molecule which is antisense to an ASPA01 nucleic acid molecule, e.g., the coding strand of an ASPA01 nucleic acid molecule. Also included within the scope of the invention are the complement strands of the nucleic acid molecules described herein.

Sequencing Errors

The sequence information as provided herein should not be so narrowly construed as to require inclusion of erroneously identified bases. The specific sequences disclosed herein can be readily used to isolate the complete gene from filamentous fungi, in particular *A. niger* which in turn can easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

Nucleic Acid Fragments, Probes and Primers

A nucleic acid molecule according to the invention may comprise only a portion or a fragment of the nucleic acid sequence shown in SEQ ID NO:1 or SEQ ID NO:2, for example a fragment which can be used as a probe or primer or a fragment encoding a portion of an ASPA01 protein. The nucleotide sequence determined from the cloning of the ASPA01 gene and cDNA allows for the generation of probes and primers designed for use in identifying and/or cloning other ASPA01 family members, as well as ASPA01 homologues from other species. The probe/primer typically comprises substantially purified oligonucleotide which typically comprises a region of nucleotide sequence that hybridizes preferably under highly stringent conditions to at least about 12 or 15, preferably about 18 or 20, preferably about 22 or 25, more preferably about 30, 35, 40, 45, 50, 55, 60, 65, or 75 or more consecutive nucleotides of a nucleotide sequence shown in SEQ ID NO:1 or SEQ ID NO: 2 or of a functional equivalent thereof.

Probes based on the ASPA01 nucleotide sequences can be used to detect transcripts or genomic ASPA01 sequences encoding the same or homologous proteins for instance in other organisms. In preferred embodiments, the probe further comprises a label group attached thereto, e.g., the label group can be a radioisotope, a fluorescent compound, an enzyme, or an enzyme cofactor. Such probes can also be used as part of a diagnostic test kit for identifying cells which express an ASPA01 protein.

Identity & Homology

The terms "homology" or "percent identity" are used interchangeably herein. For the purpose of this invention, it is defined here that in order to determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid sequences is determined using the Needleman and Wunsch (J. Mol. Biol. (48):444-453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms. In yet another embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. In another embodiment, the percent identity two amino acid or nucleotide sequence is determined using the algorithm of E. Meyers and W. Miller (CABIOS, 4:11-17 (1989) which has been incorporated into the ALIGN program (version 2.0) using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to ASPA01 nucleic acid molecules of the invention. BLAST protein searches can be performed with the XBLAST program, score=50, wordlength=3 to obtain amino acid sequences homologous to ASPA01 protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

Hybridisation

As used herein, the term "hybridizing" is intended to describe conditions for hybridization and washing under which nucleotide sequences at least about 50%, at least about 40%, at least about 70%, more preferably at least about 80%, even more preferably at least about 85% to 90%, more preferably at least 95% homologous to each other typically remain hybridized to each other.

A preferred, non-limiting example of such hybridization conditions are hybridization in 6×sodium chloride/sodium citrate (SSC) at about 45° C., followed by one or more washes in 1×SSC, 0.1% SDS at 50° C., preferably at 55° C., preferably at 60° C. and even more preferably at 65° C.

Highly stringent conditions include, for example, hybridizing at 68° C. in 5×SSC/5×Denhardt's solution/1.0% SDS and washing in 0.2×SSC/0.1% SDS at room temperature. Alternatively, washing may be performed at 42° C.

The skilled artisan will know which conditions to apply for stringent and highly stringent hybridisation conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

Obtaining Full Length DNA from Other Organisms

In a typical approach, cDNA libraries constructed from other organisms, e.g. filamentous fungi, in particular from the species *Aspergillus* can be screened.

For example, *Aspergillus* strains can be screened for homologous ASPA01 polynucleotides by Northern blot analysis. Upon detection of transcripts homologous to polynucleotides according to the invention, cDNA libraries can be constructed from RNA isolated from the appropriate strain, utilizing standard techniques well known to those of skill in the art. Alternatively, a total genomic DNA library can be screened using a probe hybridisable to an ASPA01 polynucleotide according to the invention.

Homologous gene sequences can be isolated, for example, by performing PCR using two degenerate oligonucleotide primer pools designed on the basis of nucleotide sequences as taught herein.

The template for the reaction can be cDNA obtained by reverse transcription of mRNA prepared from strains known or suspected to express a polynucleotide according to the invention. The PCR product can be subcloned and sequenced to ensure that the amplified sequences represent the sequences of a new ASPA01 nucleic acid sequence, or a functional equivalent thereof.

The PCR fragment can then be used to isolate a full length cDNA clone by a variety of known methods. For example, the amplified fragment can be labeled and used to screen a bacteriophage or cosmid cDNA library. Alternatively, the labeled fragment can be used to screen a genomic library.

PCR technology also can be used to isolate full length cDNA sequences from other organisms. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis.

The resulting RNA/DNA hybrid can then be "tailed" (e.g., with guanines) using a standard terminal transferase reaction, the hybrid can be digested with RNase H, and second strand synthesis can then be primed (e.g., with a poly-C primer). Thus, cDNA sequences upstream of the amplified fragment can easily be isolated. For a review of useful cloning strategies, see e.g., Sambrook et al., supra; and Ausubel et al., supra.

Whether or not a homologous DNA fragment encodes a functional ASPA01 protein, may easily be tested by methods known in the art.

Vectors

Another aspect of the invention pertains to vectors, preferably expression vectors, containing a nucleic acid encoding an ASPA01 protein or a functional equivalent thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signal). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, encoded by nucleic acids as described herein (e.g. ASPA01 proteins, mutant forms of ASPA01 proteins, fragments, variants or functional equivalents thereof, etc.).

The recombinant expression vectors of the invention can be designed for expression of ASPA01 proteins in prokaryotic or eukaryotic cells. For example, ASPA01 proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled person. In a specific embodiment, promoters are preferred that are capable of directing a high expression level of asparaginases in filamentous fungi. Such promoters are known in the art. The expression constructs may contain sites for transcription initiation, termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-percipitation, DEAE-dextran-mediated transfection, transduction, infection, lipofection, cationic lipid mediated transfection or electroporation. Suitable methods for transforming or transfecting host cells can be found in Sambrook, et al. (*Molecular Cloning: A Laboratory Manual*, $2^{nd}$, ed. Cold Spring Harbor Laboratory, Cold Spring Harbor Laboratory Press, Cold Spring Harbor, N.Y., 1989), Davis et al., *Basic Methods in Molecular Biology* (1986) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methatrexate. Nucleic acid encoding a selectable marker can be introduced into a host cell on the same vector as that encoding an ASPA01 protein or can be introduced on a separate vector. Cells stably transfected with the introduced nucleic acid can be identified by drug selection (e.g. cells that have incorporated the selectable marker gene will survive, while the other cells die).

Expression of proteins in prokaryotes is often carried out in *E. coli* with vectors containing constitutive or inducible promoters directing the expression of proteins.

As indicated, the expression vectors will preferably contain selectable markers. Such markers include dihydrofolate reductase or neomycin resistance for eukarotic cell culture and tetracyline or ampicillin resistance for culturing in *E. coli* and other bacteria. Representative examples of appropriate host include bacterial cells, such as *E. coli, Streptomyces* and *Salmonella typhimurium*; fungal cells, such as yeast; insect cells such as *Drosophila* S2 and *Spodoptera* Sf9; animal cells such as CHO, COS and Bowes melanoma; and plant cells. Appropriate culture media and conditions for the above-described host cells are known in the art.

Among vectors preferred for use in bacteria are pQE70, pQE60 and PQE-9, available from Qiagen; pBS vectors, Phagescript vectors, Bluescript vectors, pNH8A, pNH16A, pNH18A, pNH46A, available from Stratagene; and ptrc99a, pKK223-3, pKK233-3, pDR540, pRIT5 available from Pharmacia. Among preferred eukaryotic vectors are PWLNEO, pSV2CAT, pOG44, pZT1 and pSG available from Stratagene; and pSVK3, pBPV, pMSG and pSVL available from Pharmacia. Other suitable vectors will be readily apparent to the skilled artisan.

Among known bacterial promotors for use in the present invention include *E. coli* lacl and lacZ promoters, the T3 and T7 promoters, the gpt promoter, the lambda PR, PL promoters and the trp promoter, the HSV thymidine kinase promoter, the early and late SV40 promoters, the promoters of retroviral LTRs, such as those of the Rous sarcoma virus ("RSV"), and metallothionein promoters, such as the mouse metallothionein-l promoter.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at by 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretation signal may be incorporated into the expressed polypeptide. The signals may be endogenous to the polypeptide or they may be heterologous signals.

The polypeptide may be expressed in a modified form and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification.

Polypeptides According to the Invention

The invention provides an isolated polypeptide having the amino acid sequence according to SEQ ID NO: 3, an amino acid sequence obtainable by expressing the polynucleotide of SEQ ID NO: 1 in an appropriate host, as well as an amino acid sequence obtainable by expressing the polynucleotide sequences of SEQ ID NO: 2 in an appropriate host. Also, a peptide or polypeptide comprising a functional equivalent of the above polypeptides is comprised within the present invention. The above polypeptides are collectively comprised in the term "polypeptides according to the invention"

The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than seven amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (*Molecular Cloning: A Laboratory Manual, 2$^{nd}$*, ed. Cold Spring Harbor Laboratory, Cold Spring Harbor Laboratory Press, Cold Spring Harbor, N.Y., 1989)

By "isolated" polypeptide or protein is intended a polypeptide or protein removed from its native environment. For example, recombinantly produced polypeptides and proteins expressed in host cells are considered isolated for the purpose of the invention as are native or recombinant polypeptides which have been substantially purified by any suitable technique such as, for example, the single-step purification method disclosed in Smith and Johnson, Gene 67:31-40 (1988).

The ASPA01 asparaginase according to the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Protein Fragments

The invention also features biologically active fragments of the polypeptides according to the invention.

Biologically active fragments of a polypeptide of the invention include polypeptides comprising amino acid sequences sufficiently identical to or derived from the amino acid sequence of the ASPA01 protein (e.g., the amino acid sequence of SEQ ID NO: 3), which include fewer amino acids than the full length protein, and exhibit at least one biological activity of the corresponding full-length protein. Typically, biologically active fragments comprise a domain or motif with at least one activity of the ASPA01 protein.

A biologically active fragment of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide of the invention.

The invention also features nucleic acid fragments which encode the above biologically active fragments of the ASPA01 protein.

Functional Equivalents

The terms "functional equivalents" and "functional variants" are used interchangeably herein. Functional equivalents of ASPA01 DNA are isolated DNA fragments that encode a polypeptide that exhibits a particular function of the ASPA01 *A. niger* asparaginase as defined herein. A functional equivalent of an ASPA01 polypeptide according to the invention is a polypeptide that exhibits at least one function of an *A. niger* asparaginase as defined herein. Functional equivalents therefore also encompass biologically active fragments.

Functional protein or polypeptide equivalents may contain only conservative substitutions of one or more amino acids of SEQ ID NO: 3 or substitutions, insertions or deletions of non-essential amino acids. Accordingly, a non-essential amino acid is a residue that can be altered in SEQ ID NO: 3 without substantially altering the biological function. For example, amino acid residues that are conserved among the ASPA01 proteins of the present invention, are predicted to be particularly unamenable to alteration. Furthermore, amino acids conserved among the ASPA01 proteins according to the present invention and other asparaginases are not likely to be amenable to alteration.

The term "conservative substitution" is intended to mean that a substitution in which the amino acid residue is replaced with an amino acid residue having a similar side chain. These families are known in the art and include amino acids with basic side chains (e.g. lysine, arginine and hystidine), acidic side chains (e.g. aspartic acid, glutamic acid), uncharged polar side chains (e.g., glycine, asparagines, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine tryptophan, histidine).

Functional nucleic acid equivalents may typically contain silent mutations or mutations that do not alter the biological function of encoded polypeptide. Accordingly, the invention provides nucleic acid molecules encoding ASPA01 proteins that contain changes in amino acid residues that are not essential for a particular biological activity. Such ASPA01 proteins differ in amino acid sequence from SEQ ID NO: 3 yet retain at least one biological activity. In one embodiment the isolated nucleic acid molecule comprises a nucleotide sequence encoding a protein, wherein the protein comprises a substantially homologous amino acid sequence of at least about 40%, 65%, 70%, 75%, 80%, 85%, 90%, 95%, 96%, 97%, 98%, 99% or more homologous to the amino acid sequence shown in SEQ ID NO: 3.

For example, guidance concerning how to make phenotypically silent amino acid substitutions is provided in Bowie, J. U. et al., Science 247:1306-1310 (1990) wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As the authors state, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, supra, and the references cited therein.

An isolated nucleic acid molecule encoding an ASPA01 protein homologous to the protein according to SEQ ID NO: 3 can be created by introducing one or more nucleotide substitutions, additions or deletions into the coding nucleotide sequences according to SEQ ID NO: 1 or SEQ ID NO: 2 such that one or more amino acid substitutions, deletions or insertions are introduced into the encoded protein. Such mutations may be introduced by standard techniques, such as site-directed mutagenesis and PCR-mediated mutagenesis.

The term "functional equivalents" also encompasses orthologues of the *A. niger* ASPA01 protein. Orthologues of the *A. niger* ASPA01 protein are proteins that can be isolated from other strains or species and possess a similar or identical biological activity. Such orthologues can readily be identified as comprising an amino acid sequence that is substantially homologous to SEQ ID NO: 3.

As defined herein, the term "substantially homologous" refers to a first amino acid or nucleotide sequence which contains a sufficient or minimum number of identical or equivalent (e.g., with similar side chain) amino acids or nucleotides to a second amino acid or nucleotide sequence such that the first and the second amino acid or nucleotide sequences have a common domain. For example, amino acid or nucleotide sequences which contain a common domain having about 40%, preferably 65%, more preferably 70%, even more preferably 75%, 80%, 85%, 90%, 95%, 96%, 97%, 98% or 99% identity or more are defined herein as sufficiently identical.

Also, nucleic acids encoding other ASPA01 family members, which thus have a nucleotide sequence that differs from SEQ ID NO: 1 or SEQ ID NO: 2, are within the scope of the invention. Moreover, nucleic acids encoding ASPA01 proteins from different species which thus have a nucleotide sequence which differs from SEQ ID NO: 1 or SEQ ID NO: 2 are within the scope of the invention.

Nucleic acid molecules corresponding to variants (e.g. natural allelic variants) and homologues of the ASPA01 DNA of the invention can be isolated based on their homology to the ASPA01 nucleic acids disclosed herein using the cDNAs disclosed herein or a suitable fragment thereof, as a hybridisation probe according to standard hybridisation techniques preferably under highly stringent hybridisation conditions.

In addition to naturally occurring allelic variants of the ASPA01 sequence, the skilled person will recognise that changes can be introduced by mutation into the nucleotide sequences of SEQ ID NO: 1 or SEQ ID NO: 2 thereby leading to changes in the amino acid sequence of the ASPA01 protein without substantially altering the function of the ASPA01 protein.

In another aspect of the invention, improved ASPA01 proteins are provided. Improved ASPA01 proteins are proteins wherein at least one biological activity is improved. Such proteins may be obtained by randomly introducing mutations along all or part of the ASPA01 coding sequence, such as by saturation mutagenesis, and the resulting mutants can be expressed recombinantly and screened for biological activity. For instance, the art provides for standard assays for measuring the enzymatic activity of asparaginases and thus improved proteins may easily be selected.

In a preferred embodiment the ASPA01 protein has an amino acid sequence according to SEQ ID NO: 3. In another embodiment, the ASPA01 polypeptide is substantially homologous to the amino acid sequence according to SEQ ID NO: 3 and retains at least one biological activity of a polypeptide according to SEQ ID NO: 3, yet differs in amino acid sequence due to natural variation or mutagenesis as described above.

In a further preferred embodiment, the ASPA01 protein has an amino acid sequence encoded by an isolated nucleic acid fragment capable of hybridising to a nucleic acid according to SEQ ID NO: 1 or SEQ ID NO: 2, preferably under highly stringent hybridisation conditions.

Accordingly, the ASPA01 protein is a protein which comprises an amino acid sequence at least about 40%, 65%, 70%, 75%, 80%, 85%, 90%, 95%, 96%, 97%, 98%, 99% or more homologous to the amino acid sequence shown in SEQ ID NO: 3 and retains at least one functional activity of the polypeptide according to SEQ ID NO: 3.

Functional equivalents of a protein according to the invention can also be identified e.g. by screening combinatorial libraries of mutants, e.g. truncation mutants, of the protein of the invention for asparaginase activity. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential protein sequences is expressible as individual polypeptides. There are a variety of methods that can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the coding sequence of a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3):327-331).

In addition to the ASPA01 gene sequence shown in SEQ ID NO: 1, it will be apparent for the person skilled in the art that DNA sequence polymorphisms that may lead to changes in the amino acid sequence of the ASPA01 protein may exist within a given population. Such genetic polymorphisms may exist in cells from different populations or within a population due to natural allelic variation. Allelic variants may also include functional equivalents.

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides, can be used as hybridization probes or polymerase chain reaction (PCR) primers. Uses of the nucleic acid molecules of the present invention that do not encode a polypeptide having an ASPA01 activity include, inter alia, (1) isolating the gene encoding the ASPA01 protein, or allelic variants thereof from a cDNA library e.g. from other organisms than *A. niger*; (2) in situ hybridization (e.g. FISH) to metaphase chromosomal spreads to provide precise chromosomal location of the ASPA01 gene as described in Verma et al., Human Chromosomes: a Manual of Basic Techniques, Pergamon Press, New York (1988); (3) Northern blot analysis for detecting expression of ASPA01 mRNA in specific tissues and/or cells and 4) probes and primers that can be used as a diagnostic tool to analyse the presence of a nucleic acid hybridisable to the ASPA01 probe in a given biological (e.g. tissue) sample.

Also encompassed by the invention is a method of obtaining a functional equivalent of an ASPA01 gene or cDNA. Such a method entails obtaining a labelled probe that includes an isolated nucleic acid which encodes all or a portion of the sequence according to SEQ ID NO: 3 or a variant thereof; screening a nucleic acid fragment library with the labelled probe under conditions that allow hybridisation of the probe to nucleic acid fragments in the library, thereby forming nucleic acid duplexes, and preparing a full-length gene sequence from the nucleic acid fragments in any labelled duplex to obtain a gene related to the ASPA01 gene.

In one embodiment, an ASPA01 nucleic acid of the invention is at least 40%, 65%, 70%, 75%, 80%, 85%, 90%, 91%, 92%, 93%, 94%, 95%, 96%, 97%, 98%, 99%, or more homologous to a nucleic acid sequence shown in SEQ ID NO: 1, SEQ ID NO: 2 or the complement thereof.

In another preferred embodiment an ASPA01 polypeptide of the invention is at least 40%, 65%, 70%, 75%, 80%, 85%, 90%, 91%, 92%, 93%, 94%, 95%, 96%, 97%, 98%, 99%, or more homologous to the amino acid sequence shown in SEQ ID NO: 3.

Host Cells

In another embodiment, the invention features cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like, especially preferred are cells from filamentous fungi, in particular *Aspergillus niger*.

A host cell can be chosen that modulates the expression of the inserted sequences, or modifies and processes the gene product in a specific, desired fashion. Such modifications (e.g., glycosylation) and processing (e.g., cleavage) of protein products may facilitate optimal functioning of the protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

Host cells also include, but are not limited to, mammalian cell lines such as CHO, VERO, BHK, HeLa, COS, MDCK, 293, 3T3, WI38, and choroid plexus cell lines.

If desired, the polypeptides according to the invention can be produced by a stably-transfected cell line. A number of vectors suitable for stable transfection of mammalian cells are available to the public, methods for constructing such cell lines are also publicly known, e.g., in Ausubel et al. (supra).

In another aspect, the invention provides food products obtainable by the process of the invention as described hereinbefore or by the use of the novel asparaginase as described hereinbefore to produce food products. These food products are characterized by significantly reduced acrylamide levels in comparison with the food products obtainable by production processes that do not comprise adding one or more enzymes in an amount that is effective in reducing the level of amino acids which are involved in the formation of acrylamide during said heating step. The process according to the invention can be used to obtain a decrease of the acrylamide content of the produced food product preferably more than 50%, more preferably more than 20%, even more preferably 10% and most preferably more than 5% compared to a food product obtained with the conventional process.

MATERIALS & METHODS

Acrylamide Measurement

Sample Pretreatment 600 mg dried and homogenized sample is extracted using 5 ml of milliQ water. 1 µg of internal standard $^{13}C_3$ acrylamide in solution (CIL) is added to the extract. After 10 minutes of centrifugation (6000 rpm), 3 ml of the upper layer is brought on an Extreluut-3BT column (Merck). Using 15 ml of ethylacetate, acrylamide is eluted from the column. Ethylacetate is evaporated under a gentle stream of nitrogen down to approximately 0.5 ml.

Chromatographic Conditions

The ethylacetate solution is analysed using gas chromatography. Separation is obtained using a CP-Wax 57 (Varian) column (length 25 m, internal diameter 0.32 mm, film 1.2 µm) and helium as the carrier gas with a constant flow of 5.4 ml/min. Split-less injection of 3 µl is performed. Oven temperature is kept at 50° C. for 1 minute, after which the temperature is increased with 30° C./min towards 220° C. After 12 minutes of constant temperature of 220° C. the oven is cooled down and stabilized before next injection. Detection is performed using on-line chemical ionization mass spectrometry in positive ion mode, using methane as ionization gas. The characteristic ions m/z 72 (acrylamide) and m/z 75 ($^{13}C_3$ acrylamide) are monitored for quantification.

Used Equipment

GC: HP6890 (Hewlet Packard)

MSD (mass selective detector): HP5973 (Hewlet Packard)

Measurement of Asparaginase Activity

Asparaginase activity was measured according to Shirfrin et al. (Shirfrin, S, Parrott, C. L., and Luborsky, S. W. (1974), Journal of Biological Chemistry 249, 1445-1340).

The background of this enzyme assay is the determination of the released $NH_3$ as a result of asparaginase activity.

In order to measure released $NH_3$, the following pipette schedule was followed:

Solution A: 0.1 M citric acid+0.2 M $Na_2HPO_4$.2 $H_2O$ pH 5.5
Solution B: 0.189 M L-asparagine (Sigma)
Solution C: 0.006 M $(NH_4)_2SO_4$ (Merck)
Solution D: 25% (v/v) Trichloroacetic acid (Merck)
Solution E: Ammonia Color Reagent (Aldrich)

For asparaginase activity measurements the solutions have to be prepared freshly. In table 1 the solutions used for the calibration curve (CP=calibration point) are summarized.

TABLE 1

Calibration solution schedule

| Added solution (ml) | CP 1 | CP 2 | CP 3 | CP 4 | Reference enzyme test | Enzyme test |
|---|---|---|---|---|---|---|
| A | 1 | 1 | 1 | 1 | 1 | 1 |
| B | 0 | 0 | 0 | 0 | 0.2 | 0.2 |
| C | 0 | 0.25 | 0.5 | 1 | 0 | 0 |
| De-ionized water | 1.1 | 0.85 | 0.6 | 0.1 | 0.8 | 0.8 |
| Volume of reaction rate limiting amount of the enzyme solution | 0 | 0 | 0 | 0 | 0 | 0.1 |

Solutions according to table 1 were immediately inverted and incubated at 37° C. by inversion. After 30 minutes the reaction was terminated by the addition of 0.1 ml solution D. For the reference enzyme test 0.1 ml enzyme solution was added hereafter. The solutions were immediately mixed and centrifuged to remove any precipitate. 0.2 ml of the supernatants were pipetted to tubes containing 4.3 ml de-ionized water and 0.5 ml solution E. These mixtures were immediately mixed and after 1 minute A 436 nm was measured for the calibration samples, references and tests.

The calibration curve was made as follows:

Δ A436 nm calibration point=A 436 nm calibration point−A 436 nm calibration point 1

A standard curve is prepared by plotting the Δ A436nm of the standard versus the Ammonia (NH3) concentration.

The enzyme activity was calculated as follows:

Δ A436 nm enzyme test=A 436 nm test−A 436 nm test reference

Determine the µmoles of $NH_3$ liberated using the standard curve:

$$\text{Units/ml} = \frac{\mu\text{moles liberated } NH_3 \times V_s}{V_t \times t_i \times V_e}$$

wherein, $V_s$=Volume reaction solution (in schedule+0.1 ml solution D); 2.2 ml $V_t$=Volume of the reaction solution used for the second reaction to determine the $NH_3$; 0.2 ml $t_i$=incubation time in minutes; 30

$V_e$=volume enzyme sample to be tested; 0.1

$$\text{Specific enzyme activity} = \frac{\text{units/ml enzyme}}{\text{mg protein/ml enzyme}}$$

One unit asparaginase activity is defined 1 μmole of NH$_3$ that is liberated from L-asparagine per minute at pH 5.5 at 37° C., unless otherwise stated. Dough has a pH of about 5.5, therefore this pH is preferred in measurement. However, for other substrates with a different pH-value, this different pH is preferably used in the determination of asparaginase activity.

Amounts in ppm are based on the amount of flour, unless stated otherwise.

Materials

Asparaginase was obtained from *Escherichia coli* (Sigma, having a specific activity of 285 units/mg), *Erwinia chrysanthemi* (Sigma, having a specific activity of 100 units/mg), *Bacillus subtilis* or *Aspergillus niger* (see examples for fermentation details).

CSL medium consisted of (in amount per liter): 100 g Corn Steep Solids (Roquette), 1 g NaH$_2$PO4*H$_2$O, 0.5 g MgSO$_4$*7H$_2$O, 10 g glucose*H$_2$O and 0.25 g Basildon (antifoam). The ingredients were dissolved in demi-water and the pH was adjusted to pH 5.8 with NaOH or H$_2$SO$_4$; 100 ml flasks with baffle and foam ball were filled with 20 ml fermentation broth and sterilized for 20 minutes at 120° C. after which 200 μl of a solution containing 5000 IU/ml penicillin and 5 mg/ml Streptomycin was added to each flask after cooling to room temperature.

CSM medium consisted of (in amount per liter): 150 g maltose*H$_2$O, 60 g Soytone (pepton), 1 g NaH$_2$PO4*H$_2$O, 15 g MgSO$_4$*7H$_2$O, 0.08 g Tween 80, 0.02 g Basildon (antifoam), 20 g MES, 1 g L-arginine. The ingredients were dissolved in demi-water and the pH was adjusted to pH 6.2 with NaOH or H$_2$SO$_4$; 500 ml flasks with baffle and foam ball were filled with 100 ml fermentation broth and sterilized for 20 minutes at 120° C. after which 1 ml of a solution containing 5000 IU/ml penicillin and 5 mg/ml Streptomycin was added to each flask after cooling to room temperature.

EXAMPLE 1

Fermentation of *Aspergillus niger*

The asparaginase encoded by the nucleotide sequence as provided herein was obtained by constructing expression plasmids containing the DNA sequence, transforming an *A. niger* strain with this plasmid and growing the *Aspergillus niger* strains in the following way.

Fresh spores ($10^6$-$10^7$) of *A. niger* strains were inoculated in 20 ml CSL-medium (100 ml flask, baffle) and grown for 20-24 hours at 34° C. and 170 rpm. After inoculation of 5-10 ml CSL pre-culture in 100 ml CSM medium (500 ml flask, baffle) the strains were fermented at 34° C. and 170 rpm for 3-5 days.

Cell-free supernatants were obtained by centrifugation in 50 ml Greiner tubes (30 minutes, 5000 rpm, 4° C.), and all subsequent steps were performed on ice. The supernatants were pre-filtered over a GF/A Whatman Glass microfiber filter (150 mm Ø) to remove the larger particles, adjusted to pH 5 with 4 N KOH (if necessary) and sterile filtrated over a 0.2 μm (bottle-top) filter with suction to remove the fungal material. The supernatant were stored at 4° C. (or −20° C.).

Measurement of the *Aspergillus niger* Asparaginase Content in the Ultra-filtrate and Asparaginase Activity Step 1—Preparation of Ultra-filtrates The supernatants of the cultures as obtained in Example 1, were ultra-filtrated to obtain a higher enzyme concentration and to remove the low molecular contaminations that could interfere with the enzymatic activity determinations and the baking tests. Ultra-filtrations of 300 ml supernatant were performed in a Millipore Labscale TFF system equipped with a filter with a 10 kDa cut-off.

Depending on their colour and volume, the samples were washed 3-5 times with 10-30 ml of cold demineralised water. The final volumes of the enzyme solutions were 10-30 ml and are further referred to as "ultra-filtrates".

Step 2—Determination of the Asparaginase Concentration by A280 and HPSEC

The concentration of the *Aspergillus niger* asparaginase in the ultra-filtrate was calculated from the extinction at 280 nm (A280) attributable to the asparaginase and the calculated molecular extinction coefficient of the asparaginase. Measurement of the A280 was performed in a Uvikon XL Secomam spectrophotometer (Beun de Ronde, Abcoude, The Netherlands).

The molar extinction coefficient of an enzyme can be calculated from the number of tyrosine, tryptophan and cysteïne residues per enzyme molecule (S. C. Gill and P. H. von Hippel, Anal. Biochem. 182, 319-326 (1989)). The molar extinction coefficient of these amino acids are 1280, 5690 and 120 M$^{-1}$·cm$^{-1}$ respectively. The number of tyrosine, tryptophan and cysteïne residues in the *Aspergillus niger* asparaginase of the invention can be deduced from the protein sequences as given in SEQ ID NO: 3. The calculated extinction coefficient of the *Aspergillus niger* asparaginase of the invention is in table 2.

TABLE 2

Extinction coefficient of *A. niger* asparaginase

| Enzyme | SEQ ID NO: | # amino acids | | | Calculated M.W. (Da) | Calculated extinction coefficient at 280 nm | |
| | | Trp | Tyr | Cys | | M$^{-1}$·cm$^{-1}$ | (1 mg/ml)$^{-1}$·cm$^{-1}$ |
| Asparaginase | 3 | 0 | 9 | 2 | 39584 | 11760 | 0.3 |

The extinction of the ultra-filtrate at 280 nm (A280) that is attributable to the asparaginase depends on the purity of the enzyme sample. This purity was determined using HPSEC (High Performance Size Exclusion Chromatography) with a TSK SW-XL column (300*7.8 mm; MW range 10-300 kDa). The elution buffer consisted of 25 mM sodium phosphate buffer pH 6.0 and was used at a flow of 1 ml/min. Samples of 5-100 µl were injected. The absorbance at 280 nm was measured.

The A280 in the ultra-filtrate attributable to the asparaginase of the invention was obtained from the ratio of the peak surface of the respective asparaginase peak in the chromatogram and the total surface of the peaks absorbing at 280 nm. The asparaginase concentration in the ultra-filtrate was then calculated by multiplying the A280 of the ultra-filtrate by the ratio described above and divided by 0.3 (the calculated extinction coefficient) for each asparaginase. The solution contained 40 mg protein/ml.

Step 3—Determination of Asparaginase Activity

The *Aspergillus niger* asparaginase solution showed an activity of 40000 U/ml at pH 5.5. Therefore a specific activity of 1000 units/mg protein can be calculated taking the protein content of 40 mg/ml into account.

EXAMPLE 2 pH-Optimum of *Aspergillus niger* Asparaginase

In this example the activity was measured at various pH values. To keep the pH value constant and to correct for the buffer effect, a number of asparaginase activity measurements were performed at the same pH values in different buffers.

Three different buffers were used to measure the asparaginase activity in the pH range of 5-9:
1. citric acid/phosphate buffer (pH 5-6.2);
2. phosphate buffer (pH 8.5-7.6); and
3. tris buffer (pH 7.2-8.9).

The substrate concentration was 17.2 mM asparagine. In table 3 the asparaginase activity versus pH is displayed for asparaginase obtained from *A. niger*.

TABLE 3

*Aspergillus niger* asparaginase activity at various pH-values measured in suitable buffers. The final concentrations in the enzyme assay for the citric acid, phosphate and Tris(hydroxymethyl)aminomethane buffers are respectively 0.05, 0.1 and 0.025M.

| | Asparaginase activity (expressed in U/ml) | | |
|---|---|---|---|
| pH-value | Citric acid/phosphate buffer | Phosphate buffer | Tris-buffer |
| 5.0 | 45700 | — | — |
| 5.2 | 38000 | — | — |
| 5.4 | 40600 | — | — |
| 5.6 | 30500 | — | — |
| 5.8 | 26800 | 24200 | — |
| 6.0 | 31900 | 23000 | — |
| 6.2 | 23900 | 21800 | — |
| 6.8 | — | 14400 | — |
| 7.2 | — | 8600 | 11300 |
| 7.6 | — | — | 8700 |
| 8.0 | — | — | 6400 |
| 8.4 | — | — | 4200 |
| 8.9 | — | — | 2600 |

As is shown from the data, this *Aspergillus niger* asparaginase is very suited for baking applications, because the enzyme shows relatively high enzyme activity at the pH-value of dough which is around 5.5.

EXAMPLE 3

$K_M$ and Vmax Values for the *Escherichia coli* and *Aspergillus niger* Asparaginases Determination of $K_M$ and $V_{max}$ was performed at pH 5.5 at 37° C., by measurement of asparaginase activity of *Escherichia coli* or *Aspergillus niger* asparaginases respectively. In table 4, the results of these measurements are summarized.

TABLE 4

$K_M$ and $V_{max}$ of *Escherichia coli* or *Aspergillus niger* asparaginases

| Asparaginase origin | $V_{max}$ (U/mg) | $K_M$ (mM) |
|---|---|---|
| E. coli | 300 +/− 30 | 1.4 +/− 0.6 |
| A. niger | 1100 +/− 40 | 2.4 +/− 0.3 |

*A. niger* asparaginase shows a significantly higher activity than *E coli* asparaginase.

EXAMPLE 4

Preparation of Batard Type Bread and the Effect of *Erwinia*, *Escherichia coli* and *Aspergillus niger* Asparaginase on the Acrylamide Level in Crust and Crumb A dough was prepared from 2000 g of flour (100%), 1040 ml water (57%), 44 g fresh Konings yeast, 40 g salt (5%), 136 mg ascorbic acid (68 ppm) and the indicated amounts of asparaginase from *Erwinia* (Sigma) or *Aspergillus niger* asparaginase according to the invention. The ingredients were mixed to a dough by a spiral mixer Diosna SP 12 (2 minutes at speed 1, followed with a mixing time at speed 2 until a total energy input is reached of 85 wh). After this, the complete dough was proofed for 15 minutes at 32° C. Subsequently, dough pieces of 350 g were rounded by hand and proofed for 15 minutes at 32° C. Hereafter, the dough pieces were rounded and moulded, followed by a final proof of 75 minutes. After proofing, incisions were made in the length of the upper surface of the dough pieces with a depth of 1 cm. A sample of the dough was taken just before baking to determine the acrylamide content. The dough pieces were baked in an oven at 240° C. during 30 minutes.

Hereafter, samples were taken from the crust (the outer 2 mm) and analyzed for acrylamide as described above. The crust was taken from the upper side of the batard bread, and that part of the crust was selected that showed an average brown color, not too dark and not too white. For acrylamide-determination the average of 2 measurements of one loaf and two loaves for each condition is displayed in the tables 5, 6 and 7 below.

TABLE 5

Effect of several types of asparaginases on acrylamide formation in bread.

| | Origin of Asparaginase | Asparaginase (ppm) | Acrylamide (ppb) in crust |
|---|---|---|---|
| Loaf 1 | — | 0 | 74 |
| Loaf 2 | Erwinia | 1.75 | 51 |
| Loaf 3 | E. coli | 1.00 | 60 |
| Loaf 4 | A. niger | 0.20 | 60 |

From above table it can be concluded that the use of several types of asparaginases, including the novel ASPA01 has a decreasing effect on the amount of acrylamide formed in the crust.

TABLE 6

Effect of amount of *Erwinia* asparaginase on acrylamide formation

| | Asparaginase (ppm) | Acrylamide (ppb) In crust |
|---|---|---|
| Dough | 0 | <30 |
| Loaf 1 | 0 | 74 |
| Loaf 5 | 0.0875 | 66 |
| Loaf 6 | 0.25 | 59 |
| Loaf 2 | 1.75 | 51 |

From above table can be concluded that increasing the amount of asparaginase decreases the amount of acrylamide formed in the crust.

EXAMPLE 5

Effect of Asparaginase on Acrylamide Level in Batard Breads with Added Asparagine Dough, loaves and samples were prepared in the same manner as for example 4, whereby L-asparagine (Sigma) was added to the dough in the same step as the asparaginase was added, in the amounts as given in table 7. Acrylamide was determined in the resulting samples, which results can be found below.

TABLE 7

The effect of extra addition of asparagine on acrylamide formation in the crust.

| | Added L-asparagine (ppm) | Origin of Asparaginase | Asparaginase (ppm) | Acrylamide (ppb) in crust |
|---|---|---|---|---|
| Loaf 1 | 0 | — | 0 | 74 |
| Loaf 7 | 600 | — | 0 | 1265 |
| Loaf 8 | 600 | *Erwinia* | 0.2 | 482 |
| Loaf 9 | 600 | *A. niger* | 2 | 159 |
| Loaf 10 | 600 | *A. niger* | 5 | 105 |
| Loaf 11 | 600 | *A. niger* | 10 | 80 |
| Loaf 12 | 1500 | — | 0 | 5095 |
| Loaf 13 | 1500 | *Erwinia* | 0.5 | 3790 |

From table 7 can be concluded that addition of the amino acid asparagine to the bread significantly increases acrylamide content of the crust of the bread. This can however be decreased again with use of asparaginase.

EXAMPLE 6

Effect of Various Parameters on the Acrylamide Level in the Crust

A dough was prepared from 2000 g of whole wheat flour (100%) (Linde®—Meneba, Holland) or the normal white flour (Kolibri®—Meneba, Holland), 1140 ml water (57%), 47 g fresh Koningsgist®, 40 g salt (1.75%), 136 mg ascorbic acid (34 ppm) and the indicated amounts of L-asparagine (Sigma) and asparaginase ASPA01 obtained from *Aspergillus niger*. The ingredients were mixed to a dough by a spiral mixer Diosna SP 12 (2 minutes at speed 1, followed with a mixing time at speed 2 until a total energy input is reached of 85 wh). After this, the complete dough was proofed for 15 minutes at 32° C. Subsequently, dough pieces of 350 g were rounded by hand and proofed for 15 minutes at 32° C. Hereafter, the dough pieces were rounded and moulded, followed by a final proof of 90 minutes. After proofing, incisions were made in the length of the upper surface of the doughs with a depth of 1 cm. The dough pieces were baked in an oven. Three baking processes were used
1. 30 minutes at 240° C.
2. 20 minutes at 300° C.
3. 20 minutes at 320° C.

After baking, samples were taken from the bread crust as indicated in example 4. The results of the acrylamide analysis of the samples are given below. The amount of acrylamide in the dough was measured just before baking took place. Every figure is an average of 2 measurements of one loaf and for each condition.

TABLE 8

The effect of the baking process on the amount of acrylamide formed in the crust of bread based on normal flour, no asparagine or asparaginase added.

| Loaf number | Baking process | Acrylamide in crust (ppb) |
|---|---|---|
| 1 | 1 | 74 |
| 14 | 2 | 85 |
| 15 | 3 | 175 |

From Table 8 can be concluded that the formation of acrylamide is dependent on the applied baking process. In a hot and short baking process the formation of acrylamide is significant higher in the crust than when is baked at a lower temperature. Baking process 3 resulted very dark loaf. Therefore, no further experiments were performed under this baking condition.

TABLE 9

The effect of type of flour on the acrylamide level in the crust of bread, for baking process 1, no asparagine nor asparaginase added.

| Loaf number | Flour type | Acrylamide in crust (ppb) |
|---|---|---|
| 1 | Normal | 74 |
| 16 | Whole wheat | 227 |

From table 9 it is clear that the type of flour has an effect on the amount of acrylamide formed.

TABLE 10

The effect of sugar on the acrylamide level in the crust of bread based on normal flour and the effect of an increased amount of acrylamide on the efficiency of asparaginase of *A. niger*.

| Loaf number | Baking Process | Added sucrose (g/kg flour) | Added asparagine (ppm) | *Aspergillus niger* asparaginase (ppm) | Acrylamide in crust (ppb) |
|---|---|---|---|---|---|
| 1 | 1 | 0 | 0 | 0 | 74 |
| 17 | 1 | 250 | 0 | 0 | 220 |
| 18 | 1 | 250 | 0 | 5 | 110 |
| 19 | 1 | 250 | 600 | 0 | 847 |
| 20 | 1 | 250 | 600 | 5 | 97 |
| 14 | 2 | 0 | 0 | 0 | 85 |
| 21 | 2 | 250 | 0 | 0 | 161 |
| 22 | 2 | 250 | 0 | 5 | 120 |
| 23 | 2 | 250 | 600 | 0 | 1001 |
| 24 | 2 | 250 | 600 | 5 | 132 |

The presence of sugar stimulated the formation of acrylamide. If in addition asparagine was added, this effect was even more. When *Aspergillus niger* asparaginase was added to this sugar-rich dough system, the acrylamide level in the crust of the bread was significantly reduced. Surprisingly, for the loaves relatively rich in acrylamide, the acrylamide reduction is much more whilst using the same amount of asparaginase yielded from *Aspergillus niger*.

EXAMPLE 7

Preparation of Dutch Honey Cake

The preparation of Dutch honey cake took place in two phases. In the first phase a pre batter was made as follows: 4 kg Koekzoet® (Atlanta Dethmers B.V., Groningen—Holland) and 500 g fragmented Dutch honey cake was added to two liters of water and heated until a temperature of 116 C is reached. 5 kg rye flour was added and this is mixed until the batter is smooth. Hereafter, the dough is cooled down and stored at room temperature for 1-2 days.

Per 2750 grams of this pre-batter the following ingredients were added: 500 grams Koekzoet®, 27.5 g sifted Dutch honey cook spices, 22 g sifted Karam® Baking powder, 16.5 g Vulkaan® Baking powder (all of Atlanta Dethmers). Furthermore, various amounts of *Aspergillus niger* asparaginase was added, with an enzyme activity of 40000 U/ml (The enzyme activity was measured according to example 1, at pH 5.5).

This mixture was mixed at 104 rpm during 6 minutes in a Diosna mixer type SD 12 (Diosna, Dierks & Söhne, Osnabrück—Germany). 3250 g batter is weighted out and wetted on the outside and panned in a cake pan. Hereafter, the batter was incubated at 30° C. for 105 minutes. Hereafter, the batter was baked at 180° C. for 60 minutes. Samples of the outside layer and the inner site ("crumb") of the Dutch honey cake were analyzed on the presence of acrylamide.

After baking samples were drawn from the crust (the outer 2 mm) and the crumb (from the middle of the cake), and analyzed for acrylamide as described above. For the crust sample, crust was taken from the upper side of the cake, by selecting that part of the crust that showed an average color.

TABLE 11

The acrylamide content and the effect of various *Aspergillus niger* dosages in crust and crumb of Dutch honey cake.

| Added asparaginase (mg) | Acrylamide in sample (ppb) | | Acrylamide reduction (%)* | |
|---|---|---|---|---|
| | Crust | Crumb | Crust | Crumb |
| Reference | 1077 | 3411 | | |
| 40 | 75 | 172 | 93 | 95 |
| 100 | 85 | 158 | 92 | 95 |
| 200 | 74 | 156 | 93 | 95 |

*Acrylamide reduction was calculated by the formula below:
Acrylamide reduction =

$$\frac{\text{Acrylamide content in asparaginase-treated cake}}{\text{Acrylamide content reference}} \times 100\%$$

As is shown in this example, the addition of *Aspergillus niger* asparaginase reduced the acrylamide content to 5% compared to Dutch honey cakes that were not treated. Furthermore it is surprising that in Dutch honey cake a high level of acrylamide is found in the crumb. In all bread experiments, the amount of acrylamide in the crumb was below the detection limit of acrylamide analysis (<30 ppb), even if asparagine or sugar were added.

The invention claimed is:

1. A process for the production of a food product, wherein said process comprises contacting an intermediate form of the food product with an enzyme in an amount that is effective in modifying amino acids in said intermediate form of the food product, wherein said amino acids are associated with the formation of acrylamide when said intermediate form of the food product is exposed to heat, and wherein the enzyme is (a) an isolated asparaginase comprising an amino acid sequence at least 95% identical to SEQ ID NO: 3, or (b) an enzymatically active fragment of the isolated asparaginase of (a).

2. The process according to claim 1 wherein the food product is made from at least one plant raw material.

3. The process according to claim 2 wherein the plant raw material is cereal flour.

4. The process according to claim 1 wherein the enzyme is added as an enzyme preparation or produced in situ by a microorganism capable of producing said enzyme.

5. The process according to claim 4 wherein the enzyme preparation is derived from a microorganism.

6. The process according to claim 5 wherein the microorganism is a bacterium, a fungus or a yeast.

7. The process according to claim 2 wherein the plant raw material is wheat flour.

8. The process according to claim 1, wherein the enzyme is (a) an isolated asparaginase that comprises an amino acid sequence which is at least 99% identical to SEQ ID NO: 3, or (b) an enzymatically active fragment of the isolated asparaginase of (a).

9. The process according to claim 1, wherein the enzyme is (a) an isolated asparaginase that comprises SEQ ID NO: 3, or (b) an enzymatically active fragment of the isolated asparaginase of (a).

10. The process of claim 2, wherein the raw material is a potato, tobacco, coffee, cocoa, rice, or cereal.

11. The process according to claim 1, wherein the enzyme has an activity optimum at a pH between 5 and 6.

\* \* \* \* \*